US010437040B2

(12) United States Patent
Satake (10) Patent No.: US 10,437,040 B2
(45) Date of Patent: Oct. 8, 2019

(54) IMAGING DEVICE AND ENDOSCOPE DEVICE

(71) Applicant: OLYMPUS CORPORATION, Tokyo (JP)

(72) Inventor: Nau Satake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 287 days.

(21) Appl. No.: 15/186,794

(22) Filed: Jun. 20, 2016

(65) Prior Publication Data

US 2016/0291312 A1 Oct. 6, 2016

Related U.S. Application Data

(63) Continuation of application No. PCT/JP2014/081892, filed on Dec. 2, 2014.

(30) Foreign Application Priority Data

Dec. 20, 2013 (JP) ................. 2013-264560

(51) Int. Cl.
*A61B 1/00* (2006.01)
*A61B 1/05* (2006.01)
(Continued)

(52) U.S. Cl.
CPC .......... *G02B 23/243* (2013.01); *A61B 1/0008* (2013.01); *A61B 1/00096* (2013.01);
(Continued)

(58) Field of Classification Search
CPC ........................ A61B 1/00008; A61B 1/00096; A61B 1/042; A61B 1/05; A61B 1/051;
(Continued)

(56) References Cited

U.S. PATENT DOCUMENTS 2,465,764 A * 3/1949 Underhill, Jr. ....... G02B 7/1815
352/202
4,558,691 A 12/1985 Okada
(Continued)

FOREIGN PATENT DOCUMENTS

CN 102884470 A 1/2013
JP S57-76602 5/1982
(Continued)

OTHER PUBLICATIONS

Chinese Office Action dated Jul. 4, 2017 in Chinese Patent Application No. 201480069624.7.
(Continued)

*Primary Examiner* — Aaron B Fairchild
(74) *Attorney, Agent, or Firm* — Scully, Scott, Murphy & Presser, P.C.

(57) ABSTRACT

An imaging device includes: a holder that has a substantially hollow cylindrical shape having first and second end portions, both of the first and second end portions being opened in a longitudinal direction of the holder, the holder having a cutout portion on a side surface of the first end portion; a lens group provided inside the holder and configured to collect light incident from the second end portion of the holder; an optical member provided inside the holder and configured to transmit or reflect the light collected by the lens group; and an image sensor configured receive the light from the optical member. Part of an outer surface of the optical member is a columnar surface, and the columnar surface of the optical member abuts on an inside of the holder. Part of the image sensor is attached to the side surface of the holder through the cutout portion.

8 Claims, 12 Drawing Sheets (51) Int. Cl.
*G02B 23/24* (2006.01)
*H04N 5/225* (2006.01)
(52) U.S. Cl.
CPC .............. *A61B 1/05* (2013.01); *A61B 1/051* (2013.01); *G02B 23/2484* (2013.01); *H04N 5/2253* (2013.01); *H04N 5/2254* (2013.01); *G02B 23/2469* (2013.01); *H04N 2005/2255* (2013.01)
(58) Field of Classification Search
CPC .... A61B 1/053; H04N 5/2253; H04N 5/2254; H04N 2005/2255; H04N 5/2257
See application file for complete search history.

(56) References Cited

U.S. PATENT DOCUMENTS

| 8,917,315 | B2 | 12/2014 | Negishi | |
|---|---|---|---|---|
| 2009/0259101 | A1* | 10/2009 | Unsai | A61B 1/00096 600/110 |

FOREIGN PATENT DOCUMENTS

| JP | S60-042730 A | 3/1985 |
|---|---|---|
| JP | 2002-131656 A | 5/2002 |
| JP | 2008-079823 A | 4/2008 |
| JP | 2010-240035 A | 10/2010 |
| JP | 2011-237525 A | 11/2011 |

OTHER PUBLICATIONS

International Search Report dated Mar. 17, 2015 issued in PCT/JP2014/081892.

* cited by examiner

FIG.16

IMAGING DEVICE AND ENDOSCOPE DEVICE

CROSS REFERENCES TO RELATED APPLICATIONS

This application is a continuation of PCT international application Ser. No. PCT/JP2014/081892, filed on Dec. 2, 2014 which designates the United States, incorporated herein by reference, and which claims the benefit of priority from Japanese Patent Application No. 2013-264560, filed on Dec. 20, 2013, incorporated herein by reference.

BACKGROUND

1. Technical Field

The disclosure relates to an imaging device provided at a distal end of an insertion portion of an endoscope, the endoscope being configured to be inserted into a subject to image an inside of the subject, and relates to an endoscope device.

2. Related Art

Conventionally, endoscope devices have been widely used for various examinations in a medical field and an industrial field. Among them, endoscope devices for medical use have been widely used since observation or the like of a subject site can be performed by inserting, into a body cavity of a subject such as a patient, an elongated flexible insertion portion having a distal end portion in which an imaging device has been incorporated, and medical treatment can be performed by causing a treatment tool to project from a distal end of the insertion portion as necessary.

In recent years, due to an enlarged light receiving region and a large image sensor caused by mounting of a processing circuit, an imaging module has been proposed in which an image sensor is arranged substantially in parallel with an optical axis of an objective lens group, and light is reflected by a prism on the image sensor and received by the image sensor (for example, refer to JP 2008-79823 A and JP 2011-237525 A).

As a technique for thinning a diameter of an insertion portion of an endoscope device to reduce a burden on an examinee, an imaging device has been proposed in which a CCD unit (where an optical member is fixed to an image sensor) is fitted, directly by the optical member, into a lens frame where a lens group has been incorporated (for example, refer to JP 2002-131656 A).

SUMMARY

In some embodiments, an imaging device includes: an optical member holder that has a substantially hollow cylindrical shape having first and second end portions, both of the first and second end portions being opened in a longitudinal direction of the optical member holder, the optical member holder having a cutout portion on a side surface of the first end portion; a lens group that has a plurality of lenses and is provided inside the optical member holder, the lens group being configured to collect light incident from the second end portion of the optical member holder; an optical member provided inside the optical member holder and configured to transmit or reflect the light collected by the lens group; an image sensor having a light receiving surface to receive the light transmitted or reflected by the optical member and configured to perform a photoelectric conversion on the received light to generate an electric signal; and a substrate configured to be electrically connected to the image sensor. At least a part of an outer surface of the optical member is a columnar surface, and the columnar surface of the optical member abuts on an inside of the optical member holder. At least a part of the image sensor is attached to the side surface of the optical member holder through the cutout portion.

The above and other features, advantages and technical and industrial significance of this invention will be better understood by reading the following detailed description of presently preferred embodiments of the invention, when considered in connection with the accompanying drawings.

DETAILED DESCRIPTION

In the following, as modes for carrying out the present invention (hereinafter referred to as the "embodiment(s)"), an endoscope device provided with an imaging module will be described. The present invention is not limited by the embodiment. The same reference signs are used to designate the same elements throughout the drawings. It is noted that the drawings are only schematic, and a relation between thickness and width of each member and a ratio of each member or the like are different from actual ones. Dimensions and ratios in the different drawings may also be different from one another.

Figure 1:
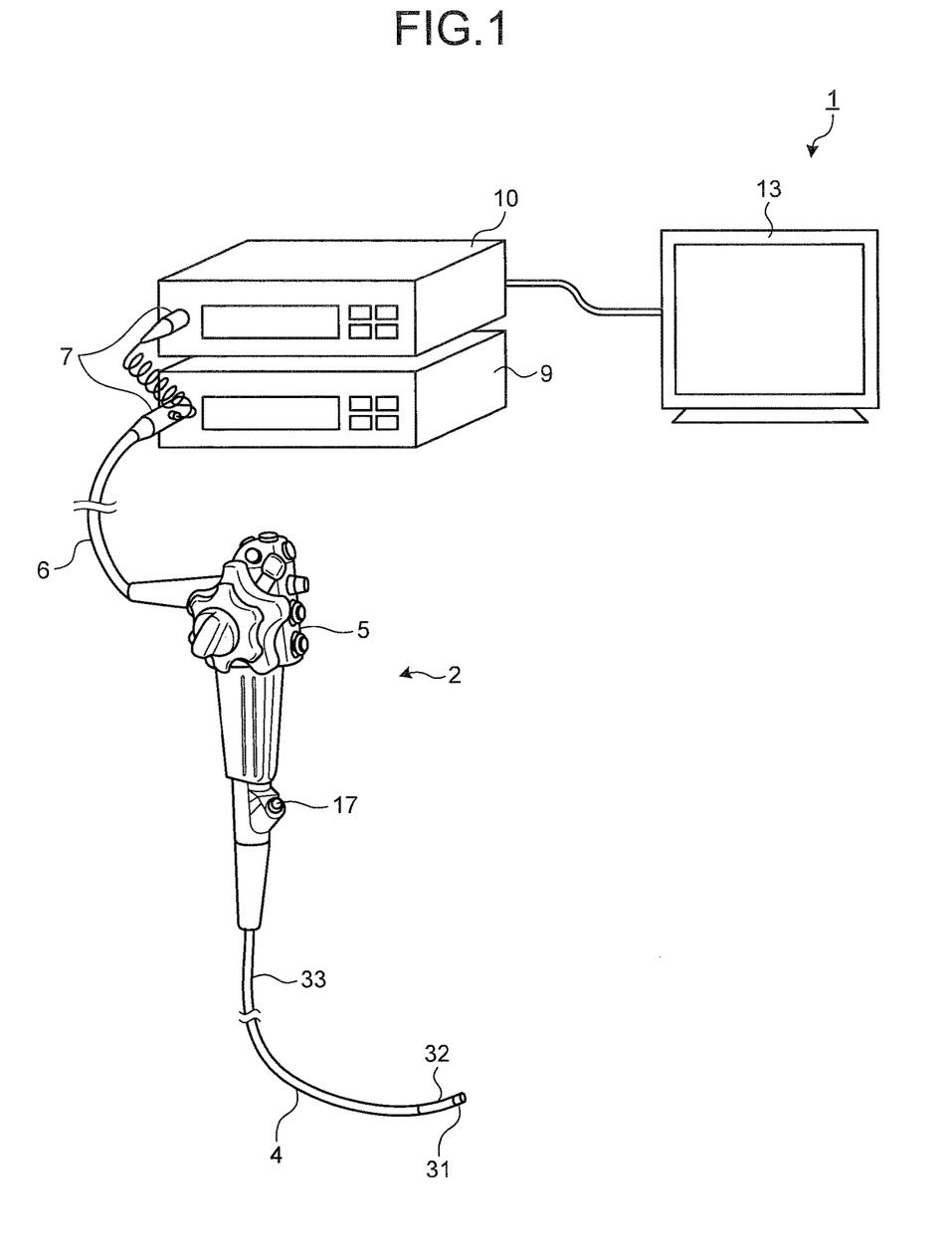
FIG. 1 is a view schematically illustrating an overall configuration of an endoscope system according to an embodiment of the present invention.

FIG. 1 is a view schematically illustrating an overall configuration of an endoscope system according to the embodiment of the present invention. As illustrated in FIG. 1, an endoscope device 1 includes an endoscope 2, a universal code 6, a connector 7, a light source device 9, a processor (control device) 10, and a display device 13.

The endoscope 2 captures an in-vivo image of a subject and outputs an imaging signal by inserting an insertion portion 4 into a body cavity of the subject. An electric cable bundle within the universal code 6 is extended to a distal end of the insertion portion 4 of the endoscope 2 and connected to an imaging device provided at a distal end portion 31 of the insertion portion 4.

The connector 7 is provided at a proximal end of the universal code 6 and connected to the light source device 9 and the processor 10. The connector 7 performs a predetermined signal process for an imaging signal output by the imaging device at the distal end portion 31 connected to the universal code 6, and subjects the imaging signal to an analog-to-digital conversion (A/D conversion) to output it as an image signal.

The light source device 9 is configured by using, for example, a white LED. Pulsed white light shed by the light source device 9 passes through the connector 7 and the universal code 6 to become illumination light radiated from the distal end of the insertion portion 4 of the endoscope 2 toward an object.

The processor 10 performs a predetermined image process on an image signal output from the connector 7, and controls the entire endoscope device 1. The display device 13 displays the image signal processed by the processor 10.

An operating unit 5 is connected to a proximal end side of the insertion portion 4 of the endoscope 2. Various buttons and knobs or the like for operating an endoscope function are provided on the operating unit 5. A treatment tool insertion opening 17 is provided in the operating unit 5. A treatment tool such as living body forceps, an electric scalpel, and an examination probe is inserted into a body cavity of a subject through the treatment tool insertion opening 17.

The insertion portion 4 includes the distal end portion 31, a bendable portion 32, and a flexible tube 33. The imaging device is provided at the distal end portion 31. The bendable portion 32 is continuously provided at a proximal end side of the distal end portion 31 and is bendable in a plurality of directions. The flexible tube 33 is continuously provided at a proximal end side of the bendable portion 32. The bendable portion 32 is bent by an operation of a knob provided on the operating unit 5, and is bendable, for example, in four directions including upward, downward, left, and right directions as a bendable wire inserted into the insertion portion 4 is pulled or loosened.

A light guide bundle (not illustrated) for delivering illumination light from the light source device 9 is arranged in the endoscope 2. An illumination lens (not illustrated) is arranged at an emission end of the illumination light delivered through the light guide bundle. The illumination lens is provided at the distal end portion 31 of the insertion portion 4, and the illumination light is radiated toward a subject.

Figure 2:
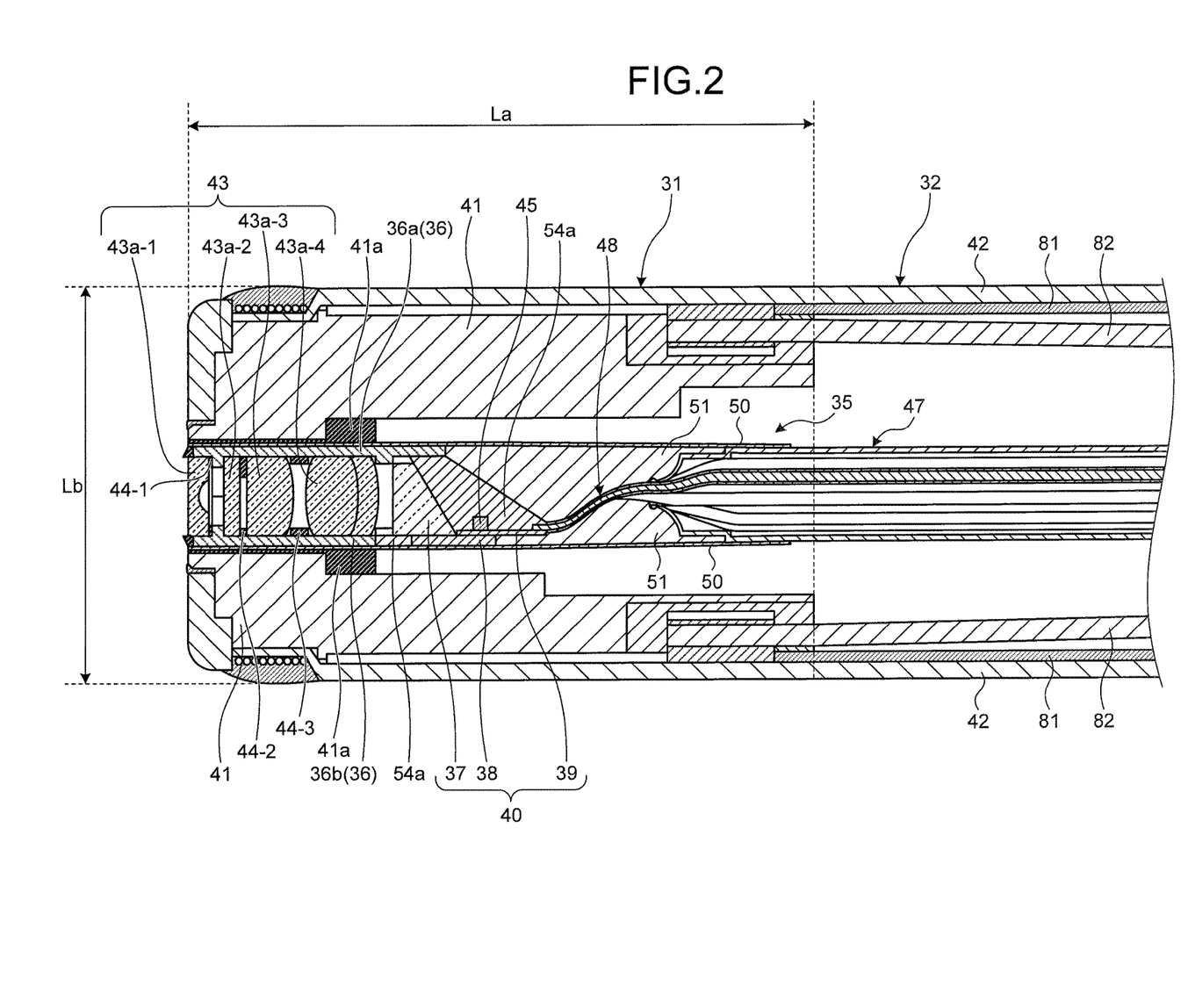
FIG. 2 is a partial cross-sectional view of a distal end of an endoscope illustrated in FIG. 1.

Next, a configuration of the distal end portion 31 of the endoscope 2 will be described in detail. FIG. 2 is a partial cross-sectional view of a distal end of the endoscope 2. FIG. 2 is the cross-sectional view cut off by a plane orthogonal to a substrate surface of the imaging device provided at the distal end portion 31 of the endoscope 2, and in parallel with an optical axis direction of incident light for the imaging device. In FIG. 2, the distal end portion 31 of the insertion portion 4 of the endoscope 2 and a part of the bendable portion 32 are illustrated.

As illustrated in FIG. 2, the bendable portion 32 is bendable in the four directions including the upward, downward, left, and right directions as a bendable wire 82, which is inserted into a bendable tube 81 arranged inside a covering tube 42 (to be described later), is pulled or loosened. An imaging device 35 is disposed inside the distal end portion 31 provided at a distal end side of the bendable portion 32.

The imaging device 35 has a lens unit 43 and an imaging unit 40 arranged at a proximal end side of the lens unit 43. The imaging device 35 is bonded to the inside of a distal end portion body 41 by an adhesive agent 41a. The distal end portion body 41 is formed of a rigid member for forming an internal space in which the imaging device 35 is housed. An outer surface of a proximal end of the distal end portion body 41 is covered with the flexible covering tube 42. A member on a proximal end side of the distal end portion body 41 is made of a flexible member such that the bendable portion 32 can be bent. The distal end portion 31 in which the distal end portion body 41 is arranged serves as a rigid portion of the insertion portion 4. A length La of the rigid portion extends from the distal end of the insertion portion 4 to the proximal end of the distal end portion body 41. A length Lb conforms to an outer diameter of the distal end of the insertion portion 4.

The lens unit 43 has a plurality of objective lenses 43a-1 to 43a-4, spacers 44-1 to 44-3 arranged between the plurality of objective lenses 43a-1 to 43a-4, and an optical member holder 36 that holds the objective lenses 43a-1 to 43a-4. The lens unit 43 is fixed to the distal end portion body 41 when a distal end of the optical member holder 36 is inserted to be fit and fixed into the distal end portion body 41.

The imaging unit 40 includes a prism 37, an image sensor 38, and a substrate 39. The prism 37 serves as an optical member that reflects light from the objective lenses 43a-1 to 43a-4 of the lens unit 43. The image sensor 38 receives the light reflected by the prism 37 and performs a photoelectric conversion to generate an electric signal. The substrate 39 is electrically connected to the image sensor 38. The image sensor 38 is bonded to the prism 37 and the substrate 39. An electronic component 45 constituting a drive circuit of the image sensor 38 is mounted on the substrate 39 of the imaging unit 40. A distal end of each signal cable 48 of an electric cable bundle 47 is connected to a proximal end of the substrate 39. An electronic component other than the electronic component constituting the drive circuit of the image sensor 38 may be mounted on the substrate 39.

A proximal end of each signal cable 48 extends in a proximal end direction of the insertion portion 4. The electric cable bundle 47 is arranged to be inserted into the insertion portion 4, and provided to extend to the connector 7 through the operating unit 5 and the universal code 6 illustrated in FIG. 1.

Light that has been incident from one end of the optical member holder 36 is collected by the objective lenses 43a-1 to 43a-4 to enter the prism 37. The image sensor 38 selected from among a CCD image sensor, a CMOS image sensor or the like is connected at a position where the image sensor 38 can receive the light radiated from the prism 37. The image sensor 38 converts the received light to an imaging signal. The imaging signal passes through the signal cable 48 connected to the substrate 39 and the connector 7, and is output to the processor 10. In this specification, one end portion of the optical member holder 36 from which light is incident (i.e., one end portion on which the objective lenses 43*a*-1 to 43*a*-4 are arranged) is referred to as a front end portion, and the other end portion of the optical member holder 36 on which the prism 37 serving as the optical member is arranged is referred to as a rear end portion.

An outer surface of the prism 37 is fitted into the optical member holder 36 on a rear end portion 36*e* side so that the optical member holder 36 holds the imaging unit 40, i.e., holds the image sensor 38 bonded to the prism 37 and the substrate 39 bonded to the image sensor 38. A space portion ranging from a position of the prism 37 in the optical member holder 36 to a rear end side of the optical member holder 36 is sealed by a sealing resin 54*a*.

Outer surfaces of the imaging unit 40 and a distal end portion of the electric cable bundle 47 are covered with a heat shrinkable tube 50 for improving resistance. The inside of the heat shrinkable tube 50 is configured such that a gap between the components is filled with an adhesive resin 51. The imaging device 35 is configured such that an outer surface of the optical member holder 36 and an outer surface of a distal end side of the heat shrinkable tube 50 are fixed to an inner peripheral surface of a distal end of the distal end portion body 41 by the adhesive agent 41*a*.

Figure 3:
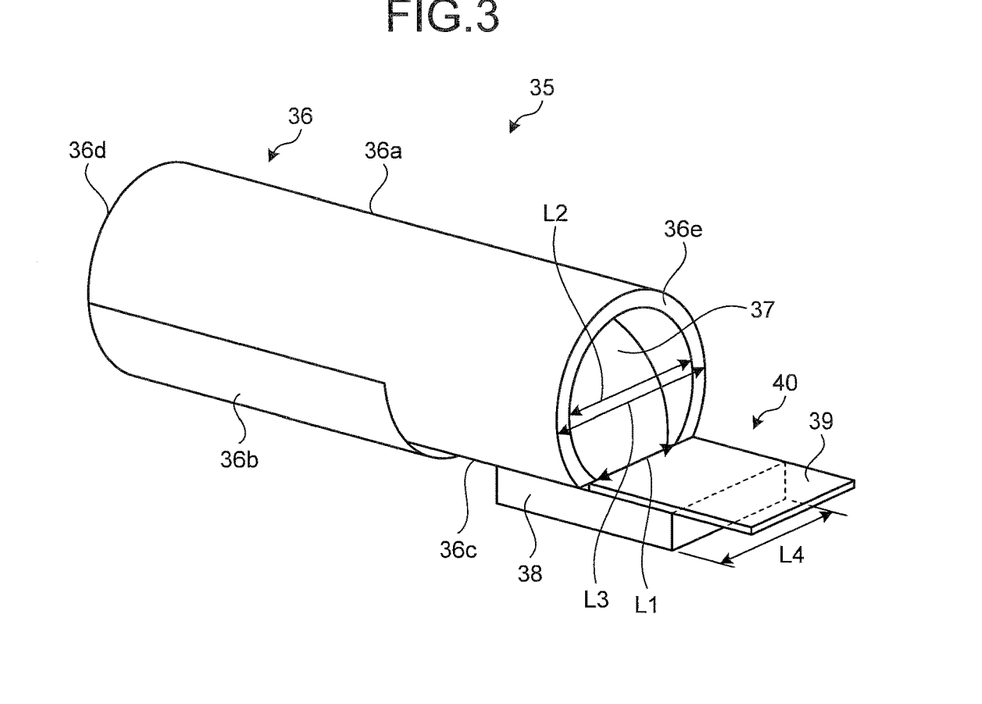
FIG. 3 is a perspective view of an imaging device illustrated in FIG. 2.
Figure 4:
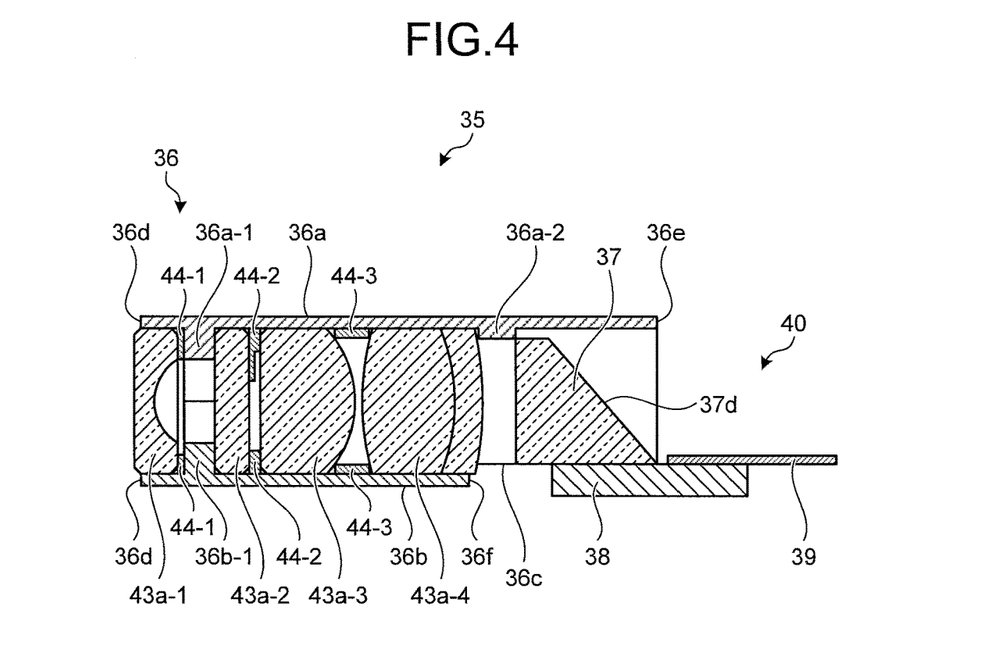
FIG. 4 is a cross-sectional view in a longitudinal direction including a vertical axis of the imaging device of FIG. 3.
Figure 5:
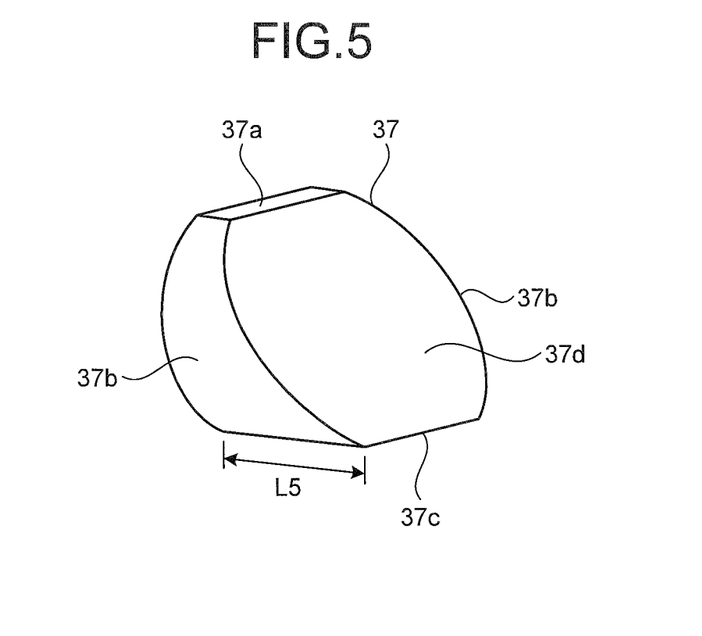
FIG. 5 is a perspective view of an optical member used in the imaging device of FIG. 2.
Figure 6:
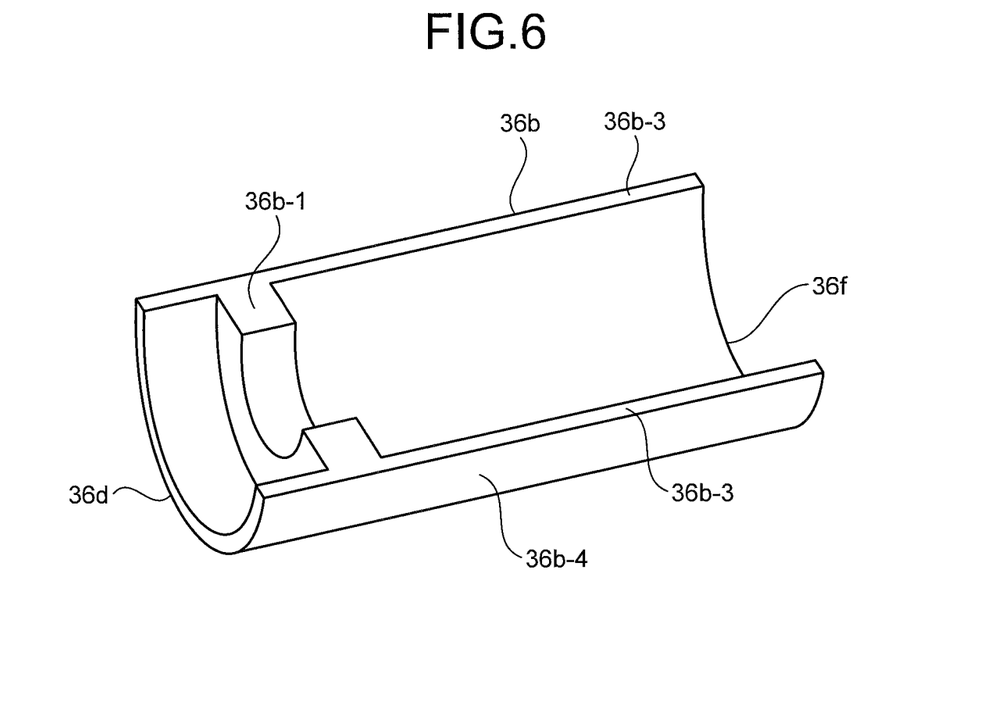
FIG. 6 is a perspective view of a holder lower frame constituting an optical member holder.

Next, the imaging device 35 will be described. FIG. 3 is a perspective view of the imaging device 35 illustrated in FIG. 2. FIG. 4 is a cross-sectional view in a longitudinal direction including a vertical axis of the imaging device 35 of FIG. 3, that is, a cross-sectional view cut off by a plane vertical to a surface of the substrate 39, and in parallel with the optical axis direction of light that enters the imaging device 35. FIG. 5 is a perspective view of the prism 37 that is the optical member used in the imaging device 35 of FIG. 2. FIG. 6 is a perspective view of a holder lower frame constituting the optical member holder 36, and FIG. 7 is a perspective view of a holder upper frame constituting the optical member holder 36.

As illustrated in FIG. 3, the optical member holder 36 has a substantially hollow cylindrical shape, both ends of which are opened. The optical member holder 36 includes a holder upper frame 36*a* and a holder lower frame 36*b* for dividing an opening of a front end portion 36*d* into vertical two parts. The objective lenses 43*a*-1 to 43*a*-4 are incorporated into the optical member holder 36 on the front end portion 36*d* side, and the prism 37 is fitted into the optical member holder 36 on the rear end portion 36*e* side, whereby the imaging unit 40 is assembled.

A positioning portion 36*b*-1 for the objective lenses 43*a*-1 to 43*a*-4 is provided inside the holder lower frame 36*b* as illustrated in FIG. 6. The positioning portion 36*b*-1 is only required to have such a structure that the objective lenses 43*a*-1 to 43*a*-4 can be prevented from being displaced in the optical axis direction, and such a size that transmission of light that comes from the front end portion 36*d* is not inhibited. A length in the optical axis direction of the holder lower frame 36*b* is preferably equal to or longer than at least a length in the optical axis direction of the objective lenses 43*a*-1 to 43*a*-4 into which the spacers 44-1 to 44-3 have been inserted. In particular, the length in the optical axis direction of the holder lower frame 36*b* is preferably sub-stantially equal to the sum of the length in the optical axis direction of the objective lenses 43*a*-1 to 43*a*-4 into which the spacers 44-1 to 44-3 have been inserted and a width in the optical axis direction of the positioning portion 36*b*-1.

Figure 7:
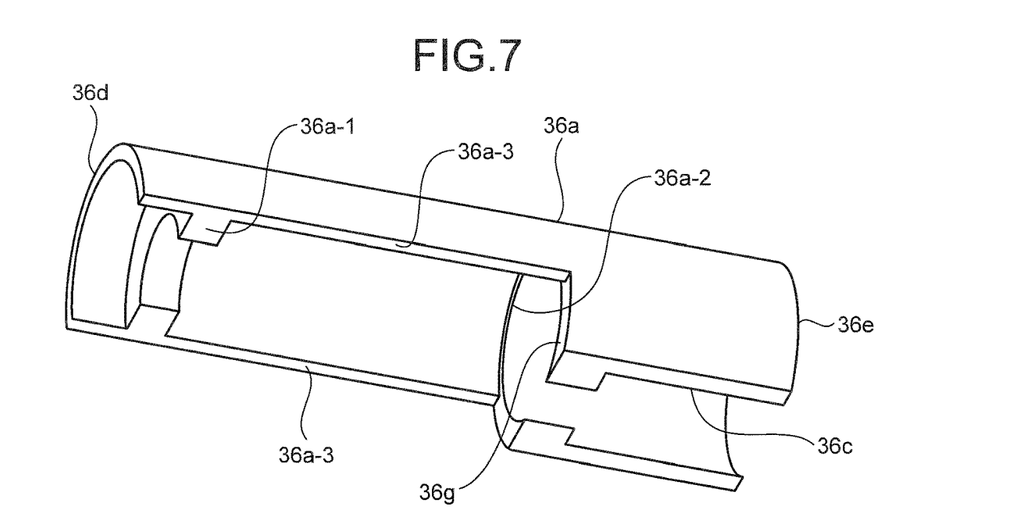
FIG. 7 is a perspective view of a holder upper frame constituting the optical member holder.

Positioning portions 36*a*-1 and 36*a*-2 for the objective lenses 43*a*-1 to 43*a*-4 are provided inside the holder upper frame 36*a* as illustrated in FIG. 7. The positioning portions 36*a*-1 and 36*a*-2 are each only required to have such a structure that the objective lenses 43*a*-1 to 43*a*-4 can be prevented from being displaced in the optical axis direction, and such a size that transmission of light that comes from the front end portion 36*d* is not inhibited. The positioning portion 36*a*-1 is formed at a position corresponding to the positioning portion 36*b*-1 of the holder lower frame 36*b*. The positioning portion 36*a*-2 also functions as a positioning portion for the imaging unit 40. A length in the optical axis direction of the holder upper frame 36*a* is preferably equal to or longer than the total sum of the length in the optical axis direction of the objective lenses 43*a*-1 to 43*a*-4 including the spacers 44-1 to 44-3 and a length L5 (refer to FIG. 5) in the optical axis direction of the prism 37. In particular, the length in the optical axis direction of the holder upper frame 36*a* is preferably longer than the sum of the length in the optical axis direction of the objective lenses 43*a*-1 to 43*a*-4 including the spacers 44-1 to 44-3, the length L5 (refer to FIG. 5) in the optical axis direction of the prism 37, and widths in the optical axis direction of the positioning portions 36*a*-1 and 36*a*-2.

The holder upper frame 36*a* on the front end portion 36*d* side has such a structure that the holder lower frame 36*b* is inverted. The holder upper frame 36*a* has a cutout portion 36*c* that is provided on the rear end portion 36*e* side and has such a structure that a side surface of a cylinder is partially cut off. A length L1 of the cutout portion 36*c* is smaller than an inner diameter L2 of the optical member holder 36. With this structure, the optical member holder 36 can hold the prism 37.

As illustrated in FIG. 5, the prism 37 has flat surface portions 37*a* and 37*c* on a top surface and a bottom surface, respectively, and has columnar side surfaces 37*b*. Although the flat surface portion 37*a* formed on the top surface facilitates application of an adhesive agent, the flat surface portion 37*a* is not necessarily required. Light that has been incident from the front end portion 36*d* of the optical member holder 36 and has been collected by the objective lenses 43*a*-1 to 43*a*-4 enters the prism 37. After that, the light is reflected by a reflection surface 37*d*, received by a light receiving portion of the image sensor 38, and subjected to the photoelectric conversion. The columnar side surfaces 37*b* of the prism 37 abut on the inside of the optical member holder 36. As illustrated in FIG. 4, it is preferable that the entire prism 37 is fitted into the optical member holder 36. This is because the imaging unit 40 is securely held by the optical member holder 36 when the entire prism 37 is fitted into the optical member holder 36.

The image sensor 38 is arranged so that a light receiving surface is in parallel with the optical axis direction of light that enters the objective lenses 43*a*-1 to 43*a*-4, and faces the prism 37. The image sensor 38 is connected to the flat surface portion 37*c* that is the bottom surface of the prism 37. A part including at least the light receiving surface of the image sensor 38 is attached to a side surface of the optical member holder 36 (36*a*) through the cutout portion 36*c* when the prism 37 is inserted from the rear end portion 36*e* of the optical member holder 36. Owing to the feature that at least a part of the image sensor 38 is attached to the side surface of the optical member holder 36 (36a), the imaging device 35 can be thinned in diameter and shortened in length.

In the embodiment, assuming that a length L4 is a length, in a direction orthogonal to the optical axis direction of the objective lenses 43a-1 to 43a-4, of a surface of the image sensor 38 brought into contact with the prism 37, in a case of using the image sensor 38 configured such that the length L4 is equal to or longer than the inner diameter L2 of the optical member holder 36, the imaging device 35 is more effectively thinned in diameter and shortened in length. The length L4 is preferably equal to or shorter than an outer diameter L3 of the optical member holder 36.

The substrate 39 is electrically connected to a part of a surface on the light receiving surface side of the image sensor 38 which is not connected to the prism 37.

Figure 8:
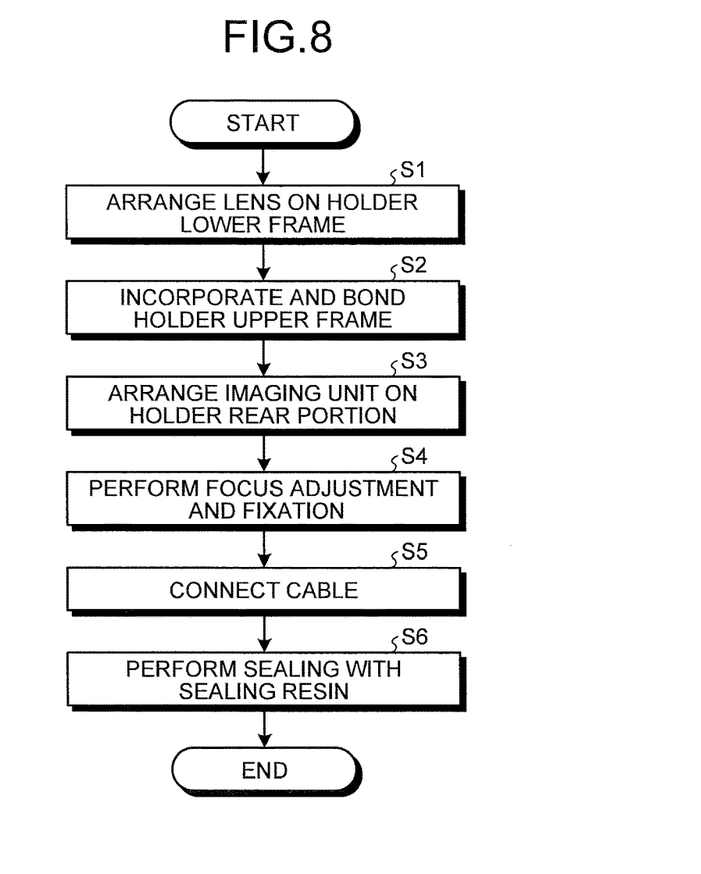
FIG. 8 is a flowchart illustrating a process for manufacturing the imaging device of FIG. 2.

Next, a method for manufacturing the imaging device 35 of the embodiment will be described. FIG. 8 is a flowchart illustrating a process for manufacturing the imaging device 35 of FIG. 2, and FIGS. 9A to 9F are schematic view for explaining the process for manufacturing the imaging device 35 of FIG. 2.

Figure 9A:
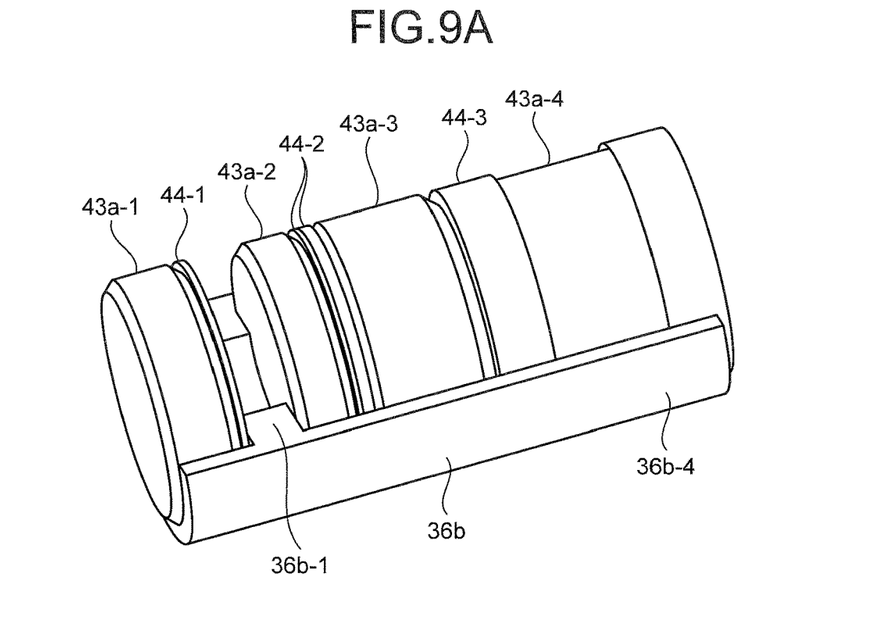
FIG. 9A is a schematic view for explaining the process for manufacturing the imaging device of FIG. 2.

First, as illustrated in FIG. 9A, the objective lenses 43a-1 to 43a-4 and the spacers 44-1 to 44-3 are arranged on the holder lower frame 36b (step S1). The objective lens 43a-1 is arranged on the front end portion 36d side of the positioning portion 36b-1, and the objective lenses 43a-2 to 43a-4 are arranged on a rear end portion 36f side of the positioning portion 36b-1. The spacers 44-1 to 44-3 are only required to be arranged after appropriately adjusted for adjusting intervals between the objective lenses 43a-1 to 43a-4.

Figure 9B:
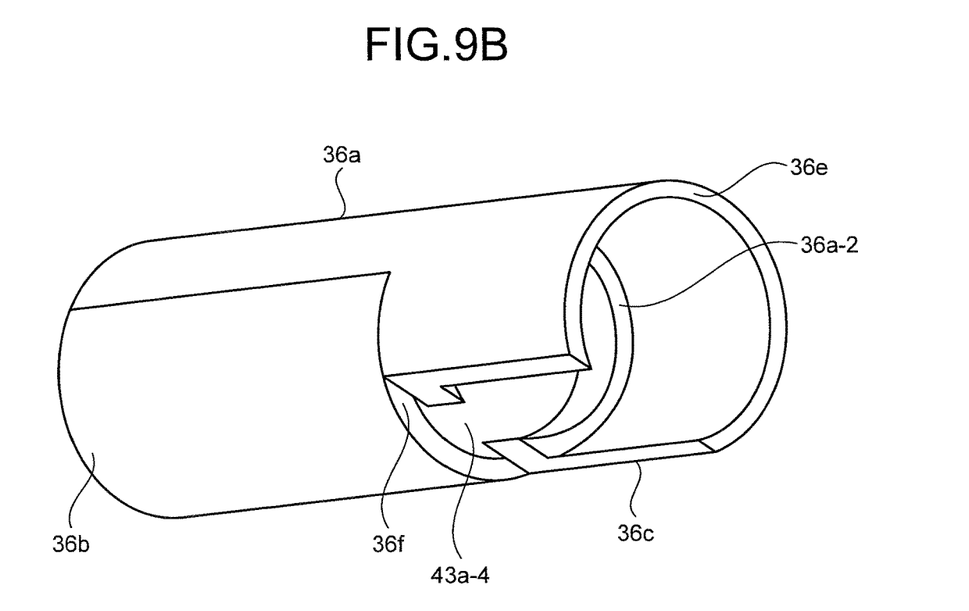
FIG. 9B is a schematic view for explaining the process for manufacturing the imaging device of FIG. 2.
Figure 9C:
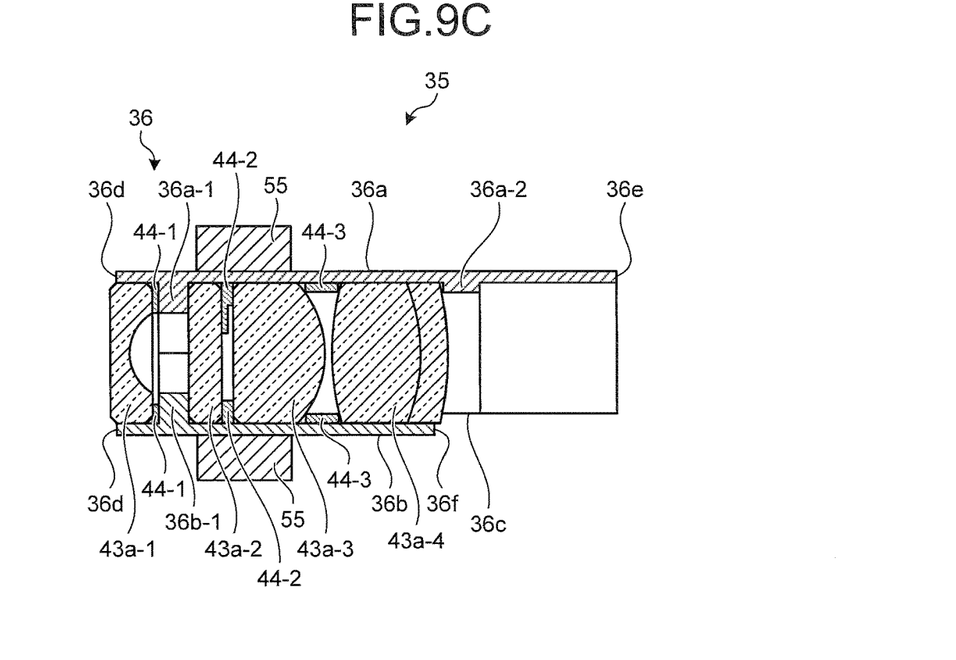
FIG. 9C is a schematic view for explaining the process for manufacturing the imaging device of FIG. 2.

After the objective lenses 43a-1 to 43a-4 are arranged on the holder lower frame 36b (step S1), as illustrated in FIG. 9B, the holder upper frame 36a is incorporated into and bonded to the holder lower frame 36b on which the objective lenses 43a-1 to 43a-4 have been arranged, so as to cap the holder lower frame 36b (step S2). FIG. 9C is a cross-sectional view of the optical member holder 36 at the time of assembling. The bonding of the holder lower frame 36b and the holder upper frame 36a is only required to be performed in such a manner that an adhesive agent is applied to contact surfaces, that is, an end surface 36a-3 and an end surface 36b-3 as well as a part of the rear end portion 36f of the holder lower frame 36b and a part of a front surface 36g of the positioning portion 36a-2 of the holder upper frame 36a, and after the assembling, the optical member holder 36 is fixed by a jig 55, and the adhesive agent is thermally hardened to finish the bonding.

In the embodiment, in order to facilitate the arrangement of the objective lenses 43a-1 to 43a-4 on the holder lower frame 36b, a side surface portion 36b-4 of the holder lower frame 36b is preferably formed in such a semi-columnar shape that a cylinder is cut off by a plane including a central axis of a circle (an center angle of the side surface portion 36b-4 is 180°. In a case where the center angle of the side surface portion 36b-4 is less than 180°, the arrangement of the objective lenses 43a-1 to 43a-4 and the spacers 44-1 to 44-3 on the holder lower frame 36b is facilitated, but the incorporation of the holder upper frame 36a might be difficult. In a case where the center angle of the side surface portion 36b-4 is greater than 180°, the arrangement of the objective lenses 43a-1 to 43a-4 and the spacers 44-1 to 44-3 on the holder lower frame 36b from above might be difficult. Therefore, the center angle of the holder lower frame 36b is preferably 180° (general tolerance, medium class).

After the holder lower frame 36b and the holder upper frame 36a are bonded together to provide the optical member holder 36 (step S2), the prism 37 of the imaging unit 40 is inserted into the optical member holder 36 from the rear end portion 36e of the optical member holder 36 until the prism 37 stops at the positioning portion 36a-2, whereby the imaging unit 40 is arranged (step S3).

Figure 9D:
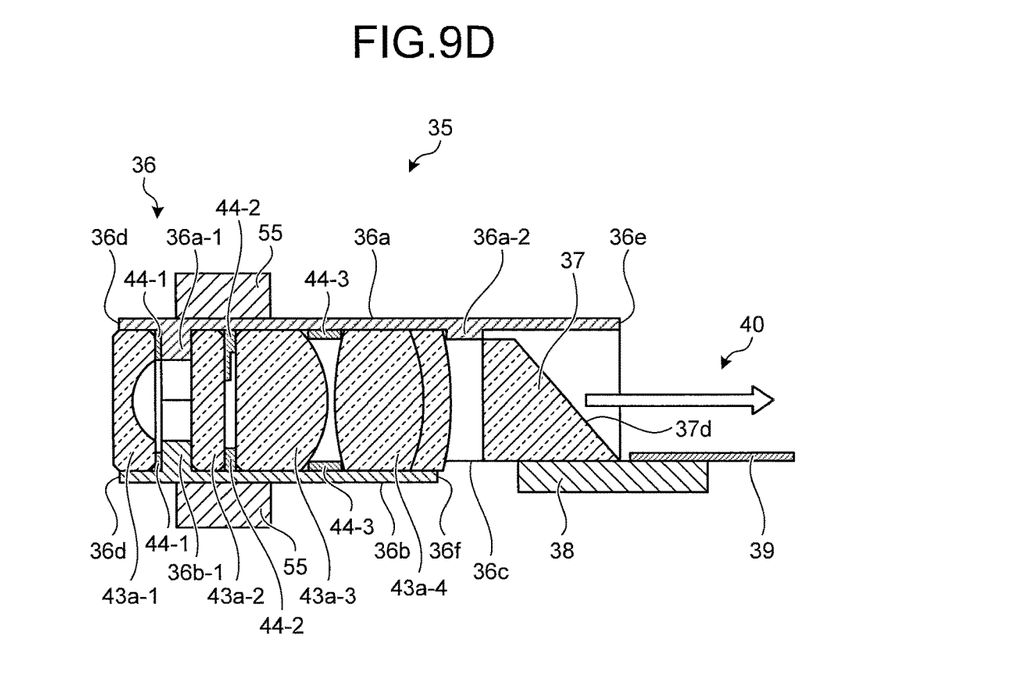
FIG. 9D is a schematic view for explaining the process for manufacturing the imaging device of FIG. 2.

After the imaging unit 40 is arranged (step S3), a focus adjustment is performed, with the optical member holder 36 fixed by the jig 55, by moving the imaging unit 40 in a direction of an arrow in FIG. 9D. An adhesive agent applied in advance to an outer surface of the prism (i.e., the flat surface portion 37a and the side surfaces 37b) is heated and hardened, whereby the outer surface of the prism 37 is bonded to an inner surface of the optical member holder 36 (step S4).

Figure 9E:
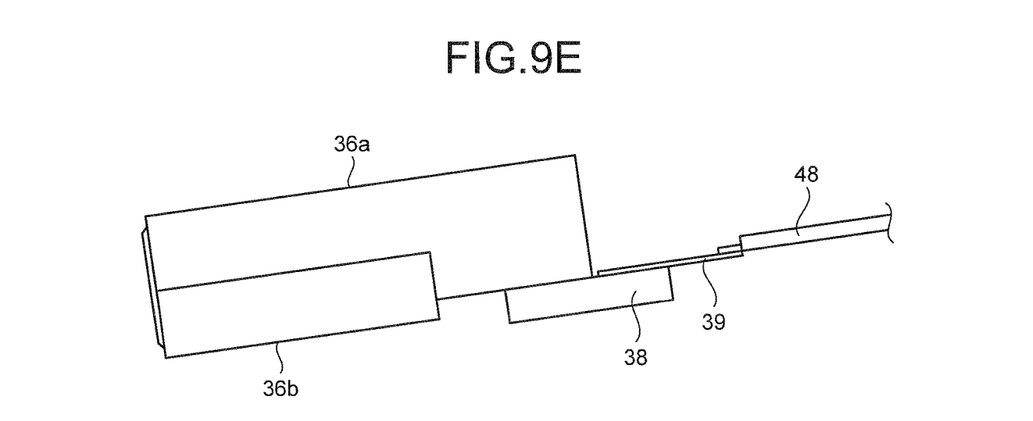
FIG. 9E is a schematic view for explaining the process for manufacturing the imaging device of FIG. 2.

After the prism 37 is fixed to the optical member holder 36 (step S4), as illustrated in FIG. 9E, the signal cable 48 is connected to a cable connection portion (not illustrated) of the substrate 39 (step S5). In the embodiment, the substrate 39 is not inserted into the optical member holder 36. However, if the cable connection portion is located posterior to the rear end portion 36e of the optical member holder 36, that is, if the cable connection portion is positioned outside of the optical member holder 36, a part of the substrate 39 may be inserted into the optical member holder 36. This is because the connection between the cable connection portion and the signal cable 48 is facilitated if the cable connection portion is located posterior to the rear end portion 36e of the optical member holder 36.

Figure 9F:
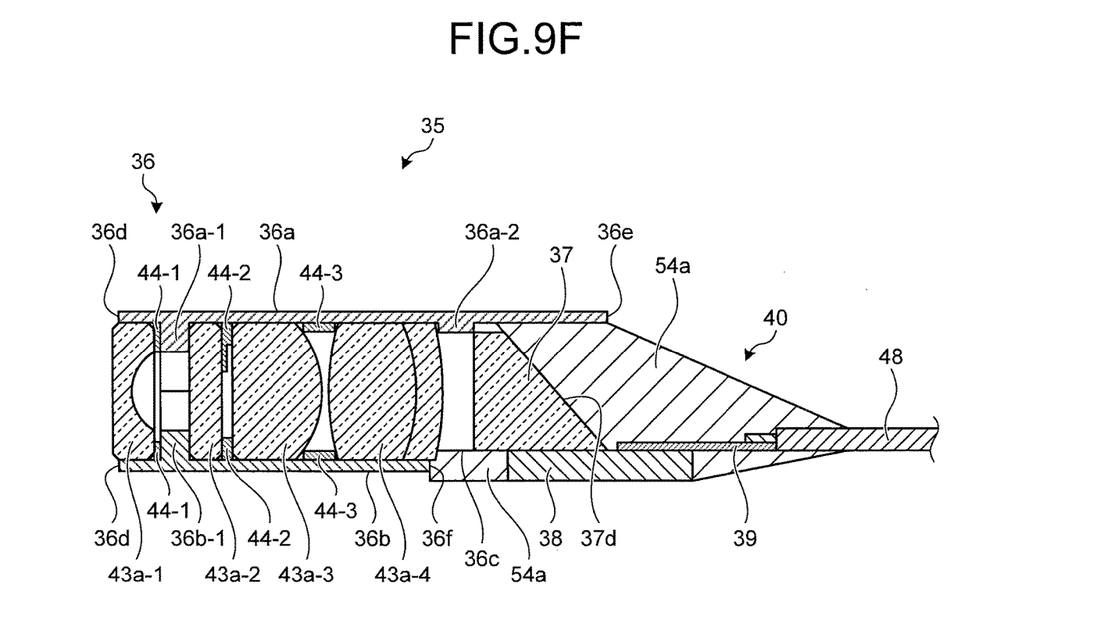
FIG. 9F is a schematic view for explaining the process for manufacturing the imaging device of FIG. 2.

After the signal cable 48 is connected (step S5), as illustrated in FIG. 9F, the sealing resin 54a is injected into a space ranging from the position of the prism 37 in the optical member holder 36 to the rear end portion 36e, the entire area of the substrate 39 including the cable connection portion, and a space between the optical member holder 36 and the image sensor 38, whereby sealing is performed (step S6). It is preferable to use the sealing resin 54a having such a viscosity that the sealing resin 54a does not enter a light path between the objective lens 43a-4 and the prism 37.

Alternatively, after the focus adjustment for the imaging unit 40 is performed, with the optical member holder 36 fixed by the jig 55, the adhesive agent applied in advance to the outer surface of the prism 37 may not be heated and hardened, and the signal cable 48 may be connected to the substrate 39, with the position of the prism 37 fixed (step S5). Then, the sealing resin 54a may be injected into the space portion in the optical member holder, and the adhesive agent and the sealing resin 54a may be simultaneously heated and hardened.

The imaging device manufactured in the above-mentioned manner can be thinned in diameter and shortened in length even when a large image sensor is used. Since the optical member holder is made up of the holder upper frame and the holder lower frame, the incorporation of the objective lenses is facilitated, and when the objective lenses are incorporated into the optical member holder, it is possible to prevent wear of the objective lenses due to rubbing of outer surfaces of the objective lenses against the inside of the holder, and deterioration in optical performance caused by the wear chips.

Figure 10:
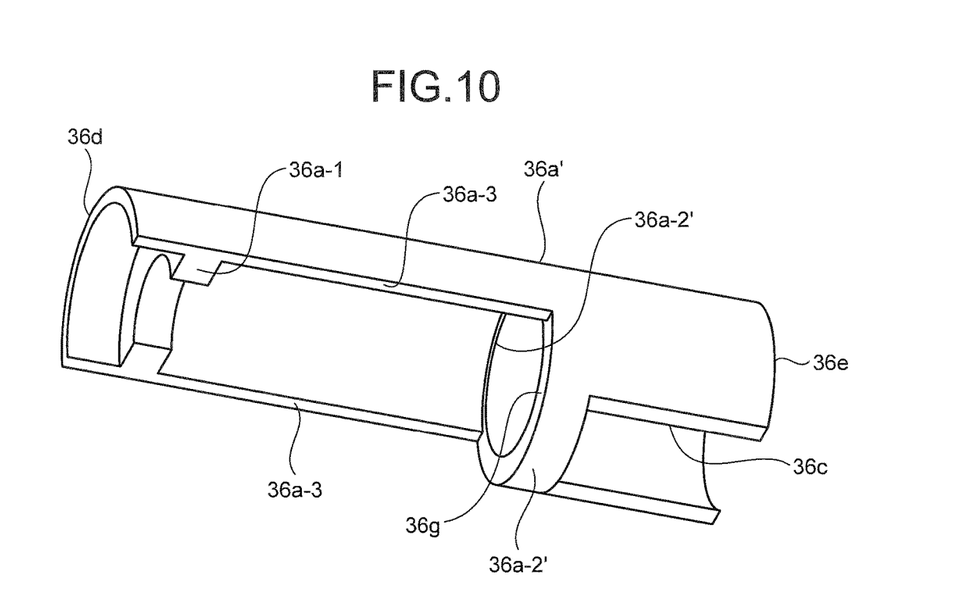
FIG. 10 is a perspective view of a holder upper frame of an optical member holder according to a first modification of the embodiment of the present invention.
Figure 11:
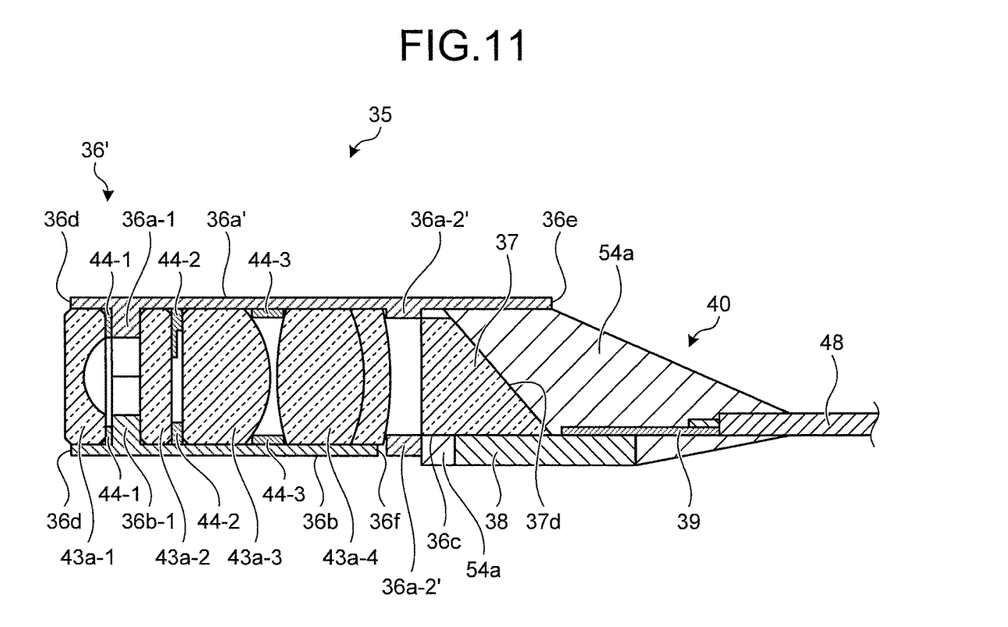
FIG. 11 is a cross-sectional view in a longitudinal direction including a vertical axis of an imaging device in which the holder upper frame of FIG. 10 is used.

In the optical member holder according to the embodiment, the cutout portion 36c formed in the holder upper frame 36a is extended up to the positioning portion 36a-2. However, the cutout portion 36c may be located posterior to the positioning portion 36a-2. FIG. 10 is a perspective view of an optical member holder according to a first modification of the embodiment of the present invention. FIG. 11 is a cross-sectional view in a longitudinal direction including a vertical axis of an imaging device in which the optical member holder of FIG. 10 is used, that is, a cross-sectional view cut off by a plane vertical to a surface of the substrate 39, and in parallel with the optical axis direction of light that enters the imaging device.

As illustrated in FIG. 10, a holder upper frame 36a' according to the first modification is different from the holder upper frame 36a according to the embodiment in that the cutout portion 36c is not formed at a positioning portion 36a-2'.

As illustrated in FIGS. 10 and 11, the holder upper frame 36a' is formed such that the positioning portion 36a-2' is circumferentially arranged. Therefore, in a case where, after the holder upper frame 36a' and the holder lower frame 36b are incorporated to provide the optical member holder 36' and the prism 37 of the imaging unit 40 is inserted from the rear end portion 36e, the sealing resin 54a is injected into a space between the optical member holder 36' and the image sensor 38, the sealing resin 54a is only required to be injected into a space between the positioning portion 36a-2' and the image sensor 38. Consequently, the sealing resin 54a is easily prevented from entering the light path between the objective lens 43a-4 and the prism 37, and use of the sealing resin 54a can be reduced. Since a contact area of the holder upper frame 36a' and the holder lower frame 36b is increased, bonding strength can be improved.

Figure 12:
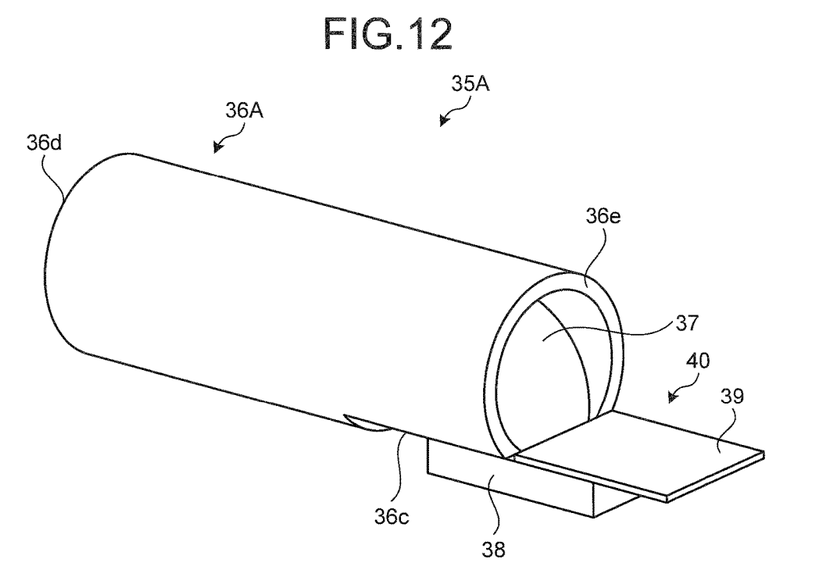
FIG. 12 is a perspective view of an optical member holder according to a second modification of the embodiment of the invention.
Figure 13:
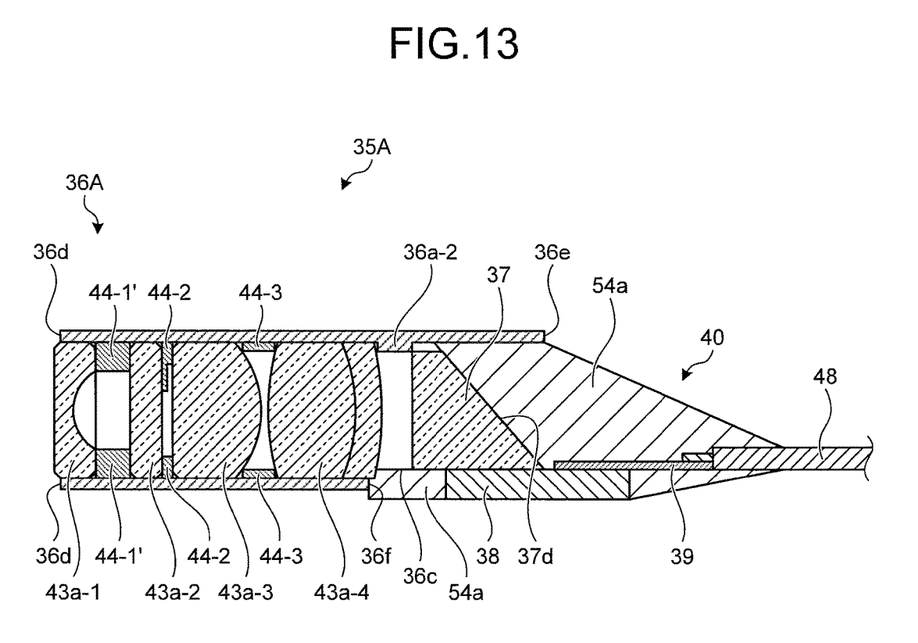
FIG. 13 is a cross-sectional view in a longitudinal direction including a vertical axis of an imaging device in which the optical member holder of FIG. 12 is used.

Although the optical member holder 36 according to the embodiment is divided into the holder upper frame 36a and the holder lower frame 36b, the optical member holder may be formed by a single member. FIG. 12 is a perspective view of an optical member holder according to a second modification of the embodiment of the invention. FIG. 13 is a cross-sectional view in a longitudinal direction including a vertical axis of an imaging device in which the optical member holder of FIG. 12 is used, that is, a cross-sectional view cut off by a plane vertical to a surface of the substrate 39, and in parallel with the optical axis direction of light that enters the imaging device.

As illustrated in FIG. 12, an optical member holder 36A according to the second modification is formed by a single member and has a substantially hollow cylindrical shape, both ends of which are opened. Although an outer shape is the same as that of the optical member holder 36 according to the embodiment, the optical member holder 36A is different from the optical member holder 36 of the embodiment in that only a single positioning portion 36A-2 is provided inside.

As illustrated in FIG. 13, the optical member holder 36A according to the second modification does not have a positioning portion (positioning portions 36a-1 and 36b-1 in the embodiment) posterior to the objective lens 43a-1. In the second modification, a spacer 44-1' is used in place of the positioning portions 36a-1 and 36b-1. In the second modification, the objective lenses 43a-1 to 43a-4 and the spacers 44-1' to 44-3 are inserted from the front end portion 36d of the optical member holder 36A, and the imaging unit 40 is inserted from the rear end portion 36e.

In the same way as the embodiment, an imaging device 35A according to the second modification can be thinned in diameter and shortened in length even when a large image sensor is used. In the second modification, the optical member holder 36A having the cutout portion 36c formed to extend to the positioning portion 36A-2 is used. In the same way as the first modification, however, such an optical member holder that the cutout portion 36c is not formed at the positioning portion 36A-2 may be used.

Figure 14:
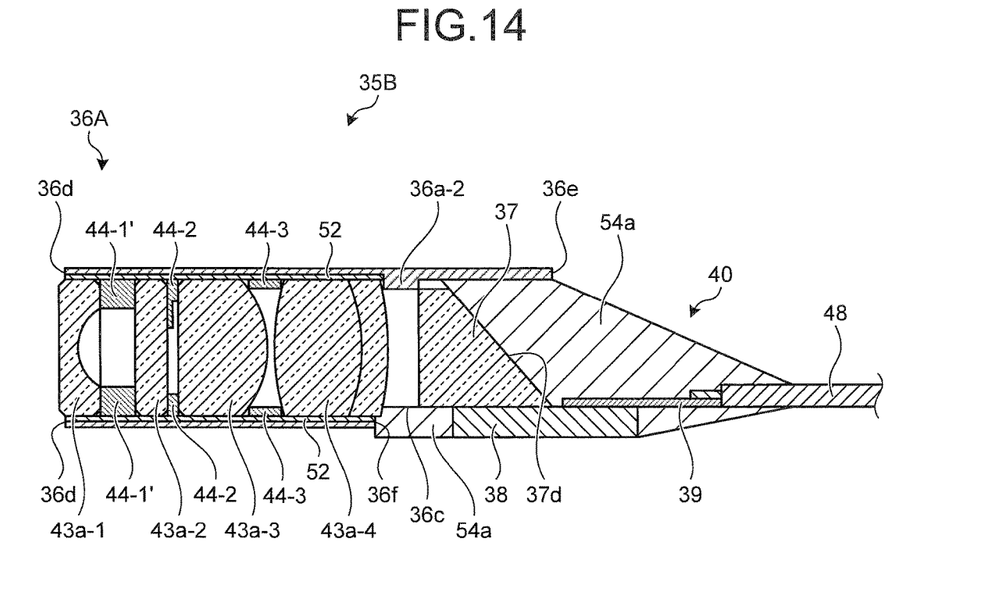
FIG. 14 is a cross-sectional view in a longitudinal direction including a vertical axis of an imaging device according to a third modification of the embodiment of the invention.

Furthermore, such a structure may be employed that a lens unit integrated by a lens frame is inserted into the optical member holder 36A according to the second modification. FIG. 14 is a cross-sectional view in a longitudinal direction including a vertical axis of an imaging device according to a third modification of the embodiment of the invention, that is, a cross-sectional view cut off by a plane vertical to a surface of the substrate 39, and in parallel with the optical axis direction of light that enters the imaging device.

An imaging device 35B according to the third modification is manufactured in such a way that after the objective lenses 43a-1 to 43a-4 and the spacers 44-1' to 44-3 are inserted into a lens frame 52 to form a lens unit, the lens unit is inserted from the front end portion 36d of the optical member holder 36A, and the imaging unit 40 is inserted from the rear end portion 36e.

In the third modification, since a material softer than that for the optical member holder 36A is employed as the lens frame, the objective lenses 43a-1 to 43a-4 and the spacers 44-1' to 44-3 can be prevented from wearing out when inserted into the lens frame. The third modification is preferable when outer diameters of the objective lenses 43a-1 to 43a-4 are smaller than an outer diameter of the imaging unit 40. In this case, the imaging device can be thinned in diameter and shortened in length. In the third modification as well, in the same way as the first modification, such an optical member holder that the cutout portion 36c is not formed at the positioning portion 36A-2 may be used.

Figure 15:
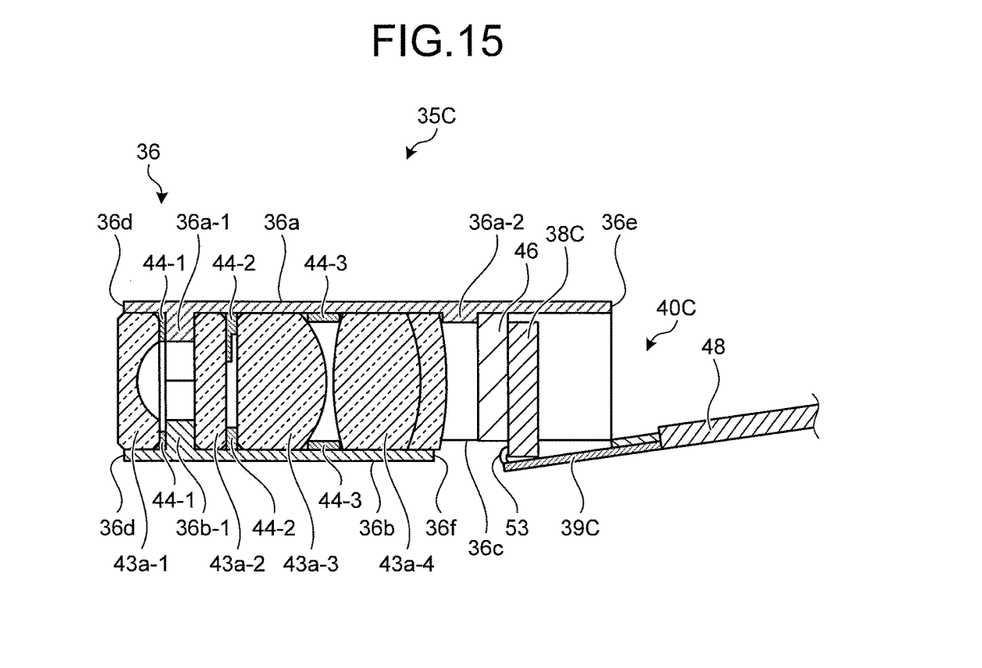
FIG. 15 is a cross-sectional view in a longitudinal direction including a vertical axis of an imaging device according to a fourth modification of the embodiment of the invention.
Figure 16:
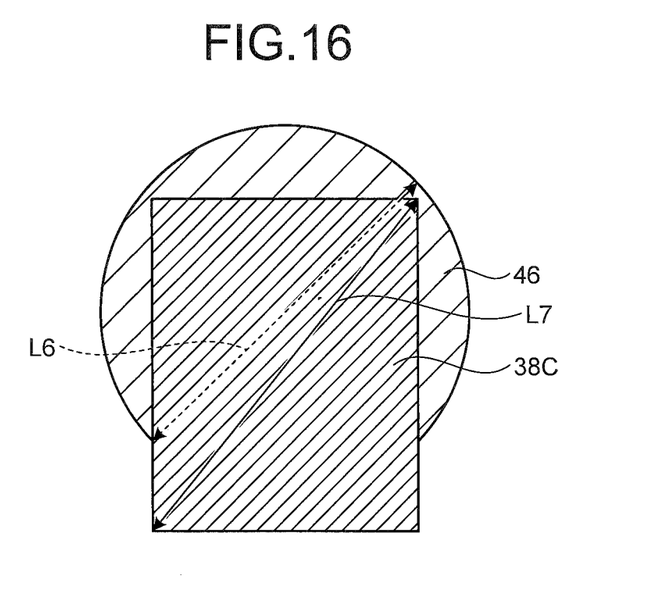
FIG. 16 is a side view of an optical member and an image sensor used in FIG. 15 viewed from the image sensor side.

Furthermore, the imaging device 35 according to the embodiment uses the imaging unit 40 configured such that the prism 37 is used as the optical member, the image sensor 38 is arranged so that the light receiving surface is in parallel with the optical axis of light that enters the objective lenses 43a-1 to 43a-4, and the image sensor 38 is connected to the flat surface portion 37c that is the bottom surface of the prism 37. However, such an imaging unit may be used that the image sensor 38 is arranged so that the light receiving surface is orthogonal to the optical axis of light that enters the objective lenses 43a-1 to 43a-4. FIG. 15 is a cross-sectional view in a longitudinal direction including a vertical axis of an imaging device according to a fourth modification of the embodiment of the present invention, that is, a cross-sectional view cut off by a vertical plane which is in parallel with the optical axis direction of light that enters the imaging device. FIG. 16 is a side view of an optical member and an image sensor used in FIG. 15 viewed from the image sensor side. The sealing resin 54a is omitted in FIG. 15.

As illustrated in FIGS. 15 and 16, an imaging unit 40C according to the fourth modification includes disk-shaped cover glass 46, an image sensor 38C, a connection electrode (not illustrated), and a substrate 39C. The image sensor 38C is arranged such that the light receiving surface is orthogonal to the optical axis of light that enters the objective lenses 43a-1 to 43a-4, and a surface of the image sensor 38C is connected to the cover glass 46 on the light receiving surface side. The connection electrode is formed on a side surface on the light receiving surface side of the image sensor 38C. The substrate 39C has an inner lead 53. In the fourth modification, the cover glass 46 functions as the optical member. The cover glass 46 is cut so as to have a flat surface on the cutout portion 36c side. In an imaging device 35C according to the fourth modification, the objective lenses 43a-1 to 43a-4 collect incident light from the front end portion 36d of the optical member holder 36, the cover glass 46 transmits the light from the objective lenses 43a-1 to 43a-4, and the image sensor 38C receives the light transmitted by the cover glass 46 to perform the photoelectric conversion.

In the fourth modification, when the cover glass 46 is inserted from the rear end portion 36e of the optical member holder 36, an outer surface (arc-like portion) of the cover glass 46 abuts on the inside of the optical member holder 36, whereby the optical member holder 36 holds the imaging unit 40C. When the cover glass 46 is inserted into the optical member holder 36, a projection portion in the optical axis direction of the cover glass 46 of the image sensor 38C is incorporated into the optical member holder 36, and a portion other than the projection portion in the optical axis direction of the cover glass 46 of the image sensor 38C is incorporated in a lower part of the optical member holder 36 through the cutout portion 36c. Owing to this structure, the imaging device 35C can be thinned in diameter and shortened in length. Although the sealing resin 54a is omitted from FIG. 16, a space portion ranging from a position of the cover glass 46 and the image sensor 38C in the optical member holder 36 to a rear end side of the optical member holder 36, and a gap between the rear end portion 36f of the holder lower frame 36b and the cover glass 46, the image sensor 38C, and the substrate 39C are sealed by the sealing resin 54a.

In the fourth modification, the image sensor 38C may have such a size as to be received in the projection portion in the optical axis direction of the cover glass 46. However, assuming that a length L7 is a length of a diagonal line of a surface including a light receiving portion, in a case of using the image sensor 38C configured such that the length L7 is greater than a diameter L6 of the cover glass 46, the imaging device 35C is more effectively thinned in diameter and shortened in length. In the fourth modification as well, such an optical member holder that the cutout portion 36c is not formed at the positioning portion 36a-2 can be used in the same way as the first modification, and an integrated optical member holder of the second modification can also be used.

According to some embodiments, since a cutout portion is provided at a rear end portion of an optical member holder, an optical member of an imaging unit can be provided together with a lens group, and an imaging device can be thinned in diameter and shortened in length.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   an optical member holder that has a hollow cylindrical shape having first and second end portions, both of the first and second end portions being opened in a longitudinal direction of the optical member holder, the optical member holder having a cutout portion defining a cutout surface on an outside surface of the first end portion, the cutout surface extending along a longitudinal direction of the optical member holder;
   a lens group that has a plurality of lenses and is provided inside the optical member holder, the lens group being configured to collect light incident from the second end portion of the optical member holder;
   an optical member provided inside the optical member holder and configured to transmit or reflect the light collected by the lens group;
   an image sensor having a light receiving surface to receive the light transmitted or reflected by the optical member and configured to perform a photoelectric conversion on the received light to generate an electric signal; and
   a substrate configured to be electrically connected to the image sensor, wherein at least a part of an outer surface of the optical member is a columnar surface, and the columnar surface of the optical member abuts on an inside of the optical member holder, and
   at least a part of the image sensor contacting the cutout surface of the optical member holder.

2. The imaging device according to claim 1, wherein the optical member is a prism, and
   the image sensor is arranged such that the light receiving surface is parallel to an optical axis direction of the lens group, and faces the optical member.

3. The imaging device according to claim 1, wherein the optical member holder includes a holder lower frame and a holder upper frame.

4. The imaging device according to claim 3, further comprising a spacer inserted between at least any two of the plurality of lenses, wherein
   a length of the holder lower frame is equal to or longer than at least a length in an optical axis direction of the lens group, and
   a length of the holder upper frame is equal to or longer than sum of the length in the optical axis direction of the lens group and a length in an optical axis direction of the optical member.

5. The imaging device according to claim 1, wherein the optical member holder includes at least one positioning portion inside the optical member holder to position at least one of the lens group and the optical member.

6. The imaging device according to claim 1, further comprising a cable configured to be electrically connected to the substrate, wherein
   a connection portion between the substrate and the cable is provided on the substrate, and is located posterior to the first end portion of the optical member holder.

7. The imaging device according to claim 1, a further comprising a sealing resin disposed inside the first end portion of the optical member holder from the optical member toward a rear end of the optical member holder.

8. An endoscope device comprising the imaging device according to claim 1 that is configured to be inserted into a living body to image an inside of the living body.

* * * * *